(12) United States Patent
Vucica et al.

(10) Patent No.: US 9,890,203 B2
(45) Date of Patent: Feb. 13, 2018

(54) PROCESS FOR PREPARING APOLIPOPROTEIN A-I (APO A-I)

(71) Applicant: CSL LIMITED, Parkville, Victoria (AU)

(72) Inventors: Yvonne Vucica, Bern (CH); Gary Lee Warren, Bourbonnais, IL (US)

(73) Assignee: CSL LIMITED, Parkville, Victoria (AU)

( * ) Notice: Subject to any disclaimer, the term of this patent is extended or adjusted under 35 U.S.C. 154(b) by 0 days.

(21) Appl. No.: 14/893,178

(22) PCT Filed: Jun. 5, 2014

(86) PCT No.: PCT/AU2014/000584
§ 371 (c)(1),
(2) Date: Nov. 23, 2015

(87) PCT Pub. No.: WO2014/194362
PCT Pub. Date: Dec. 11, 2014

(65) Prior Publication Data
US 2016/0176946 A1    Jun. 23, 2016

Related U.S. Application Data

(60) Provisional application No. 61/831,304, filed on Jun. 5, 2013.

(51) Int. Cl.
*A61K 38/17* (2006.01)
*C07K 14/775* (2006.01)
*C07K 1/30* (2006.01)
*A61K 38/00* (2006.01)

(52) U.S. Cl.
CPC ............ *C07K 14/775* (2013.01); *C07K 1/30* (2013.01); *A61K 38/00* (2013.01); *A61K 38/17* (2013.01)

(58) Field of Classification Search
CPC ...... A61K 38/00; A61K 38/17; C07K 14/775; C07K 1/30
See application file for complete search history.

(56) References Cited

U.S. PATENT DOCUMENTS

| | | | |
|---|---|---|---|
| 5,089,602 A | 2/1992 | Isliker et al. | |
| 8,962,802 B2 | 2/2015 | Brinkman et al. | |
| 9,125,943 B2 | 9/2015 | Vucica et al. | |
| 2002/0156007 A1* | 10/2002 | Graversen | A61K 38/47 435/69.1 |
| 2008/0138394 A1* | 6/2008 | Kim | A61K 31/7088 424/450 |
| 2011/0087008 A1* | 4/2011 | Brinkman | C07K 14/775 530/359 |

FOREIGN PATENT DOCUMENTS

| | | |
|---|---|---|
| KR | 10-0992488 B | 11/2010 |
| WO | WO 98/07751 A1 | 2/1998 |
| WO | WO 2009/025754 A2 | 2/2009 |
| WO | WO 2014/066943 A1 | 5/2014 |

OTHER PUBLICATIONS

Rahman, "IgA| Immunoglobulin A Class", https://www.bio-rad-antibodies.com/iga-immunoglobulin-a-antibody.html; accessed Feb. 5, 2017; 2 Pages.*
Lerch et al., "Production and Characterization of a Reconstituted High Density Lipoprotein for Therapeutic Applications," Vox Sanguinis, vol. 71, pp. 155-164, 1996.
Lerch et al., "Isolation and properties of Apolipoprotein A for Therapeutic Use," Protides of the Biological Fluids, vol. 36, pp. 409-416, 1989.
International Search Report issued on Aug. 25, 2014 in application No. PCT/AU2014/000584.
Cohn et al., "Preparation and Properties of Serum and Plasma Proteins. IV. A System for the Separation into Fractions of the Protein and Lipoprotein Components of Biological Tissues and Fluids," Separation into Fractions of Protein and Lipoprotein Components, vol. 68, pp. 459-475, Mar. 1940.
Oncley et al., "The Separation of the Antibodies, Isogglutinins, Prothrombin, Plasminogen and $\beta_1$-Lipoprotein into Subfractions of Human Plasma," Subfractions of Human Plasma, vol. 71, pp. 541-550, Feb. 1949.
Nitschmann et al., "Simplified Procedures for the Extraction of Human albumin and γ-globulin derived from blood plasma using the alcohol precipitation," Helvetica Chimica Acta., vol. 37, No. 107, pp. 866-873, 1954.
Kistler et al., "Large Scale Production of Human Plasma Fractions," Vox Sang., vol. 7, pp. 414-424, 1962.
Kim et al., "Manufacturing and Shelf Stability of Reconstituted High-density Lipoprotein for Infusion Therapy," Biotechnology and Bioprocess Engineering, vol. 16, pp. 785-792, 2011.
European Pharmacopoeia, "2.6.22. Activated Coagulation Factors," Ph. Eur. Monograph, p. 209, Jan. 2008.
Peitsch, M. et al. "A Purification Method for Apolipoprotein A-I and A-ll". Analytical Biochemistry, vol. 178, 1989, pp. 301-305.

(Continued)

*Primary Examiner* — Lianko G Garyu
(74) *Attorney, Agent, or Firm* — Foley & Lardner LLP

(57) ABSTRACT

The present invention relates to processes of obtaining Apo A-1 from an Apo A-1 containing protein fraction (A), comprising suspending—the Apo A-1 containing protein fraction (A) in a buffer solution (B), removing impurities from the suspension while keeping the Apo A-1 proteins solubilized, followed by precipitating Apo A~I from the suspension and collecting the Apo A-1 precipitate. Apo A-I obtained by such processes, reconstituted HDL obtained from such Apo A-1, and pharmaceutical compositions comprising such Apo A-I and/or reconstituted HDL also are provided.

18 Claims, 5 Drawing Sheets

(56) References Cited

OTHER PUBLICATIONS

Extended European Search Report dated Oct. 21, 2016 in related EP Appl. No. 14808213.4 (10 pgs.)

* cited by examiner

A)

B)

PROCESS FOR PREPARING APOLIPOPROTEIN A-I (APO A-I)

FIELD

The present invention relates to a process of recovering Apolipoprotein A-I (Apo A-I) from an Apo A-I containing protein fraction.

BACKGROUND

Human Apolipoprotein A-I is the major protein component of (HDL), which is an important lipoprotein in blood. It is synthesized by the liver and intestine and is responsible for the physiological function of HDL in the blood; the removal of cholesterol from peripheral tissues, carrying it back either to the liver or to other lipoproteins, by a mechanism known as "reverse cholesterol transport" (RCT).

The clear correlation between elevated levels of serum cholesterol and the development of coronary heart disease has been repeatedly confirmed, based on epidemiological and longitudinal studies.

Hence, Apo A-I in HDL is thought to have an anti-inflammatory function and to restrain the occurrence and development of CHD. Furthermore, Apo A-I has shown to decrease the Low Density Lipoproteins (LDL) level in the blood and is known to bind to endotoxins, thus having a major role in the anti-endotoxin function of HDL.

The "protective" role of HDL and Apo A-I as its major component has been confirmed in a number of studies making Apo A-I a promising candidate (particularly as part of a reconstituted HDL) for applications in atherosclerosis treatment, acute coronary syndrome treatment (ACS), anti-inflammation treatment, antitoxin treatment, liver-targeting drugs, etc.

Human blood plasma is nowadays collected in large amounts and processed to individual fractions some of which contain apolipoprotein A-I. The fractions may be produced by ethanol fractionation according to a procedure originally developed in the United States and known as Cohn or Cohn-Oncley methods [E. J. Cohn et al., J. Am. Chem. Soc. 68, 459-475, 1946; J. L. Oncley et al., J. Am. Chem. Soc. 71, 541-550, 1949]. Plasma fractions containing apolipoproteins may also be produced by a variant of this method, the Kistler-Nitschmann procedure [H. Nitschmann et al., Helv. Chim. Acta 37, 866-873, 1954; P. Kistler and H. Nitschmann, Vox Sang 7, 414-424, 1962]. Both methods are based on differential precipitation in alcohol.

Various approaches have been described in the literature to recover apolipoprotein A-I from ethanol precipitation fractions:

U.S. Pat. No. 5,089,602 for instance, relates to the preparation of apolipoproteins from fractions of human blood plasma or serum by resuspending the fractions in an aqueous buffer solution in the pH range 3 to 5 or 6 to 9. Undesirable contaminants are precipitated by addition of a short chain aliphatic alcohol. Use is made of buffers containing high ethanol concentrations (68-96% ethanol) for precipitating contaminants. Potential aggregation of lipoproteins is inhibited through elevated temperature, slightly alkaline pH, or by the addition of chaotropic agents or surface-active substances, which is subsequently removed by gel filtration. An anion-exchange chromatography step is included to bind the contaminants, while the apolipoproteins pass through.

Kim et al., *Manufacturing and Shelf Stability of Reconstituted High-density Lipoprotein for Infusion Therapy*, Biotechnology and Bioprocess Engineering 16, 785-792 (2011) disclose the use of extraction buffers containing urea in a concentration of 6 M.

A combination of the two above mentioned methods is described in WO 98/07751 for recovering apolipoprotein A (Apo A-I) or apolipoprotein E (ApoE) from human plasma. Said document discloses a process comprising at least one pre-purification step through the use of an extraction buffer containing 8 M urea and a further purification step using anion-exchange chromatography. In WO 98/07751, 1% recovery of Apo A-I resulted from experiments using an extraction buffer comprising 20% ethanol. WO2009/025754 teaches methods to separate Apo A-I from alpha-1 antitrypsin including the use of lower ethanol concentrations (8 to 14%) to precipitate Apo A-I.

Other methods such as ultra-speed centrifuge and high performance liquid chromatography (HPLC) are also used to recover Apo A-I. However, the preparation of Apo A-I is extremely time-consuming and only minor quantities of Apo A-I can be prepared by these methods. These methods are therefore not suitable for an industrial production of Apo A-I.

Thus, there remains a need for a method for extracting and recovering Apo A-I from Apo A-I containing protein fractions, which is suitable for large-scale production and which allows for acquiring Apo A-I in a high yield.

SUMMARY

Provided herein are processes of obtaining Apo A-I from an Apo A-I containing protein fraction (A), comprising a) suspending the Apo A-I containing protein fraction in a buffer solution comprising 15 to 30% of a linear or branched $C_1$ to $C_4$ alcohol (w/w) to form a suspension, wherein the suspended Apo A-I containing protein fraction (A) has a pH in the range from 6.4 to 10.0, (b) removing impurities from the suspension while keeping the Apo A-I proteins solubilized, (c) precipitating Apo A-I from the suspension, and (d) collecting the Apo A-I precipitate.

In some embodiments, the buffer solution comprises 201 of the linear or branched $C_1$ to $C_4$ alcohol (w/w). In some embodiments, the suspended Apo A-I containing protein fraction (A) has a pH in the range from 8.1 to 8.5. In some embodiments, the the suspended Apo A-I containing protein fraction (A) has a pH in the range from 7.0 to 7.6. In some embodiments the buffer solution comprises 5 mM to 35 mM $NaHCO_3$. In some embodiments, the linear or branched $C_1$ to $C_4$ alcohol is ethanol.

In some embodiments, the volume ratio of Apo A-I protein fraction to buffer solution at step (a) is from 1:1 to 1:5.

In some embodiments, the suspension formed at step (a) has a conductivity of less than 5 mS/cm.

In some embodiments, impurities are removed in step (b) by precipitation by adding linear or branched $C_1$ to $C_4$ alcohol to an alcohol concentration of 45 to 65% (w/w). In some embodiments, the linear or branched $C_1$ to $C_4$ alcohol added at step (b) has a temperature of about −5° C. to 15° C. In some embodiments, the impurities precipitated at step (b) are removed from the suspension by filtration, centrifugation, decantation, ultrafiltration and/or sedimentation.

In some embodiments, in step (c), the pH of the suspension is adjusted in the range from 4.6 to 5.6. In some embodiments, in step (c), the suspension has a temperature of −2 to 20° C. for precipitation of Apo A-I.

In accordance with any embodiments, the process may further comprise step (e), wherein the collected Apo A-I precipitate is delipidated, such as through addition of alcohol for example ethanol at a concentration from within the range from about 40% to about 96% ethanol (w/w). In particular embodiments the collected Apo A-I precipitate is delipidated through the addition of ethanol to a concentration of about 40%, or of about 50%. The ethanol can be any pharmaceutical grade ethanol. In particular embodiments of the invention the ethanol is a 95% pharmaceutical grade ethanol (3A containing 5% methanol).

In accordance with some embodiments, the process yields purified Apo A-I at a yield of at least 0.50 g/L plasma.

In another aspect of the present invention, there is provided a purified Apo A-I comprising: (a) less than 0.3 mg of IgA per gram of Apo A-I.

Also provided is Apo A-I obtained by any process as described herein, pharmaceutical compositions comprising such Apo A-I and a pharmaceutically acceptable carrier or diluent and/or methods of producing such compositions.

Also provided is reconstituted HDL prepared from Apo A-I obtained by any process as described herein, pharmaceutical compositions comprising such reconstituted HDL and a pharmaceutically acceptable carrier or diluent and/or methods of producing reconstituted HDL and/or compositions comprising same.

BRIEF DESCRIPTION OF THE DRAWINGS

FIG. 1 shows that the yield of Apo A-I obtained from plasma is maximized when using a buffer solution (B) comprising lower concentrations of ethanol.

FIG. 2 shows that the yield of Apo A-I obtained from plasma is maximized when using a buffer solution (B) comprising ethanol in a concentration within the range of 15 and 30%.

FIG. 3 further shows the influence of the pH on the Apo A-I yield when using an ethanol concentration within the range from 20 to 50%. The yield is maximized when Apo A-I is suspended in a buffer solution (B) comprising an ethanol in a concentration within the range of 15 and 30% and a pH of the suspension within the range from 6.4 to 10.0.

FIG. 4 shows that the yield of Apo A-I obtained from plasma is maximized when using a buffer solution (B) comprising ethanol in a concentration within the range of 15 and 30%.

FIG. 5 shows that minimizing the cool down time during the resolubilization of Fraction IV material reduces proteolytic activity and clotting factor activation in the purified Apo A-I preparations.

DETAILED DESCRIPTION

Figure 1:
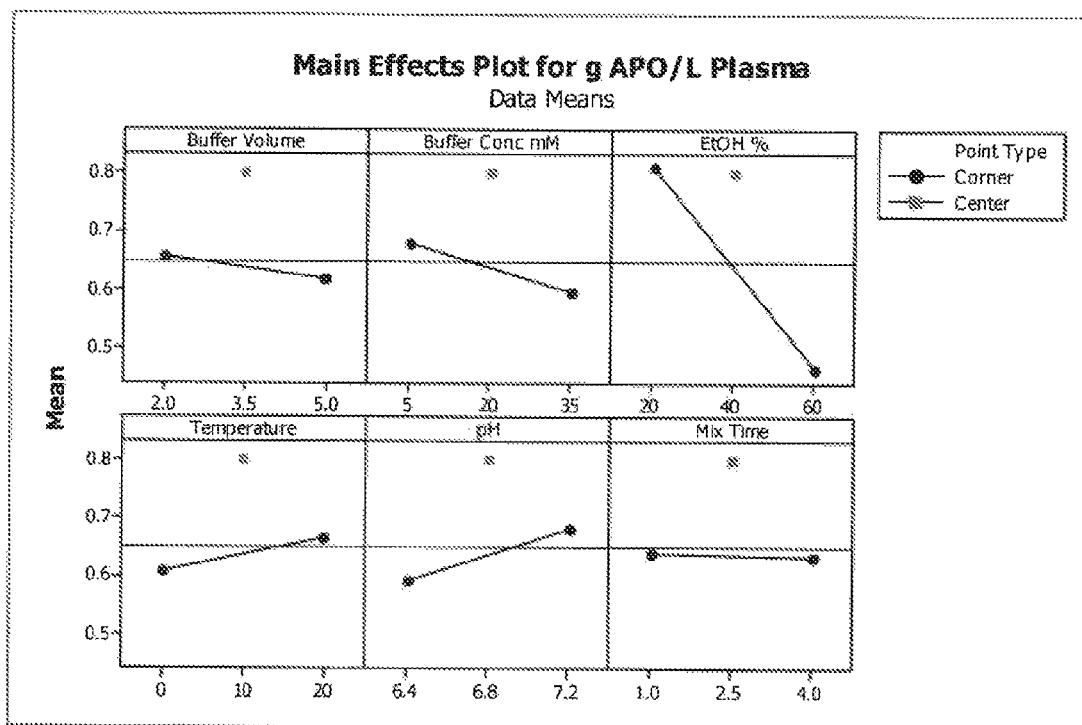
FIG. 1: Influence of buffer volume, buffer concentration, ethanol concentration, temperature, pH and mixing time on Apo A-I yield.

Described herein are processes of obtaining Apo A-I from an Apo A-I containing protein fraction (A), comprising the steps of: (a) suspending an Apo A-I containing protein as fraction (A) in a buffer solution (B) comprising 15 to 30% of a linear or branched C1 to C4 alcohol (w/w), wherein the suspended Apo A-I containing protein fraction (A) has a pH in the range from 6.4 to 10.0, and (b) removing impurities from the suspension while keeping the Apo A-I proteins solubilized. In particular embodiments, step (b) is followed by (c) precipitating Apo A-I from the suspension, and, optionally, (d) collecting the Apo A-I precipitate.

In the context of the processes described herein, the term "suspending an Apo A-I containing protein fraction" means solubilising the Apo A-I containing protein fraction, thus bringing into solution at least a major part of the protein fraction.

Surprisingly, it has been found that if the Apo A-I containing protein fraction (A) is solubilized in a volume of buffer solution (B) comprising 15 to 30% of a linear or branched C1 to C4 alcohol (w/w) wherein the suspended Apo A-I containing protein fraction (A) has a pH in the range from 6.4 to 10.0, including 6.4 to 7.5 or 8.1 to 8.5, much more Apo A-I proteins can be suspended in a given buffer volume than with the previously known methods, even without the addition of chaotropic substances such as urea. Therefore, the amount of Apo A-I obtained from the starting fraction (A) can be increased substantially as compared to previously known methods.

These findings are particularly noteworthy, since according to the state of the art, alcohol concentrations in the range of 15 to 30% (w/w) are insufficient for solubilizing the Apo A-I proteins, leading to very low yields.

Contrary to these expectations, in some embodiments, the unique combination of pH and alcohol concentration according to the processes described herein achieves purified Apo A-I with a yield of Apo A-I of at least 0.50 grams/Liter of plasma (g/L plasma). In some embodiments, at least 0.60 g/L plasma of Apo A-I is obtained by the processes described herein (at step b). In contrast, when the amount of ethanol exceeds 30% w/w then the Apo A-I recovery is lower. For example, at 45% w/w the recovery of Apo A-I is approximately 0.12 g/L plasma, indicating that the methods described herein are able to increase Apo A-I recoveries by at least 300%.

The processes described herein provide a simpler and more economical way of solubilizing Apo A-I than suggested in the related art. Also, the reduced explosion hazard due to the use of lower concentrations of the linear or branched $C_1$ to $C_4$ alcohol offers advantages of lower costs with regard to the construction of the manufacturing unit for the precipitation step.

Furthermore, in embodiments where the pH range of the suspended Apo A-I containing protein fraction (A) is from 6.4 to 9.0, this pH level is believed to prevent deamidation of the proteins, thereby leading to a reduced risk that the resulting biopharmaceutical drugs will be immunogenic. In some embodiments the suspended Apo A-I containing protein fraction (A) has a pH in the range from 6.4 to 9.0, including from 7.2 to 8.8, or from 8.0 to 8.6, or from 8.1 to 8.5, or from 8.2 to 8.4, or from 6.4 to 7.4.

The processes described herein are fast, robust, specific and safe, and provide an improved yield and purity of the product of interest during processing. Therefore, the processes described herein are particularly well suited for use in large-scale purification of Apo A-I. Suitable for large-scale purification in the context of this disclosure means purification starting from tens of kilograms of a starting material such as a human plasma fraction, for example starting from 50 kilograms or more, such as 500 kilograms, of a Apo A-I protein containing starting fraction.

As used herein, "plasma" refers to liquid blood components and includes plasma derivatives, and plasma-containing compositions.

The present processes thereby facilitate an improved and acceptable balance between yield of product and economy involved, compared to the conventionally used methods.

The processes will now be illustrated with regard to specific embodiments. It is to be understood from the following description that the invention includes all permutations and combinations of the different embodiments of the different steps, components, and parameters illustrated below.

Any starting material comprising Apo A-I can be used in the methods described herein, such as any starting material containing a substantial amount of Apo A-I, such as any unpurified mixtures of proteins containing a substantial amount Apo A-I.

The term "Apo A-I" refers to Apo A-I proteins and fractions thereof. Typically, the apolipoprotein A-I is either a plasma-derived or recombinant apolipoprotein A-I such as Apo A-I, pro-apo-A1 or a variant such as Apo A-I Milano or so called oxidation resistant forms such as 4WF. In some embodiments, the apolipoprotein A-I is plasma derived Apo A-I. Also contemplated are biologically-active fragments of the apolipoprotein A-I. Fragments may be naturally occurring, chemical synthetic or recombinant.

According to specific embodiments, the starting material is an Apo A-I containing protein fraction (A), such as one selected from a fraction of human plasma such as plasma fraction IV-I or IV (sometimes also referred to as Precipitate IV or similar), for instance, obtained by cold ethanol fractionation of human plasma according to the Cohn Fractionation method or the Kistler and Nitschmann method or other similar methods. Other examples can include ammonium sulfate precipitates which contain Apo A-I. When using plasma fraction IV as its raw material, the processes described herein offer the advantage of making full use of plasma resources. In particular embodiments, the starting material is a Fraction IV or a Cohn Fraction $IV_1$ or a Cohn Fraction $IV_4$ or a similar Fraction. In further specific embodiments, the starting material is derived from a Fraction IV precipitate. Other Apo A-I containing protein fractions (A) can include those in which alpha-1-antitrypsin (AAT) has been previously removed for separate manufacture into an AAT therapeutic product, such as Zemaira™. Examples of such Apo A-I containing protein fractions are described in WO 2009/025754. The AAT can be separated from the Apo A-I by i) treating a starting human plasma fraction comprising Apo A-I and AAT to separate an Apo A-I containing fraction from an AAT containing fraction, comprising a) optionally treating the starting human plasma fraction which is used as the starting material such that both Apo A-I and AAT are solubilized; b) precipitating the solubilized Apo A-I by adding ethanol to a concentration of 8-14% v/v and adjusting the pH to about 5 to about 6 so that Apo A-I precipitates and AAT remains in solution; and c) separating precipitated Apo A-I from the solution containing AAT. This precipitated Apo A-I, in particular embodiments of the present invention, is the Apo A-I containing protein fraction (A). The starting human plasma fraction comprising AAT and Apo A-I can be selected from one or more of Fraction IV-I or IV (sometimes also referred to as Precipitate IV or similar) obtained by cold ethanol fractionation of human plasma according to the Cohn Fractionation method or the Kistler and Nitschmann method or other similar methods. In some instances these fractions may be referred to as Cohn fractions IV, precipitates from Kistler-Nitschmann supernatants A and A+1 (e.g. Precipitate A+IV). Other examples can include ammonium sulfate precipitates which contain AAT and Apo A-I. In some embodiments the Apo A-I containing protein fraction comprises a finely divided silicon dioxide, such as Aerosil™.

The Apo A-I containing protein fraction (A) is suspended in a buffer solution (B) comprising 15 to 30% of a linear or branched C1 to C4 alcohol (w/w) and the suspended Apo A-I containing protein fraction (A) has a pH in the range from 6.4 to 10.0. In some embodiments the pH of the suspended Apo A-I containing protein fraction (A) is adjusted in the range 6.4 to 10.0 after the Apo A-I containing protein fraction (A) has been suspended in the buffer solution (B).

In some embodiments the buffer solution (B) for solubilizing the Apo A-I protein fraction (A) comprises 16 to 28%, or 17 to 26%, or 18 to 24% or 19 to 22% of the linear or branched $C_1$ to $C_4$ alcohol (w/w).

In some embodiments, the buffer solution (B) for solubilizing the Apo A-I protein fraction (A) comprises 20% of the linear or branched $C_1$ to $C_4$ alcohol (w/w). This low alcohol concentration compared to prior art methods is not only beneficial from an economical point of view but also allows for solubilizing an increased amount of the Apo A-I protein fraction (A), increasing the overall yield of purified Apo A-I from a given amount of starting material.

In some embodiments, the buffer solution (B) has a pH in the range from 6.4 to 10.0, including from 6.4 to 9.0 or, from 7.2 to 8.8 or from 8.0 to 8.6 or from 6.4 to 7.4. In more specific embodiments, the pH of the buffer solution (B) is in the range from 8.1 to 8.5, such as 8.3. These pH ranges are believed to minimize deamination and denaturation of Apo A-I proteins.

In other more specific embodiments, the pH of the buffer solution (B) is in the range from 7.0 to 7.4, such as 7.3. This pH range is believed to minimize deamination and denaturation of Apo A-I proteins.

The buffer solution (B) can be prepared with any suitable salt. One suitable salt for preparing the buffer solution (B) is $NaHCO_3$. $NaHCO_3$ is low in price and commercially available in large amounts, and thus is well suited for industrial scale applications. In some embodiments, the buffer solution (B) comprises 5 mM to 35 mM $NaHCO_3$, such as 15 mM or 25 mM $NaHCO_3$. These buffer conditions have been shown to be particularly effective for solubilizing the Apo A-I protein fraction (A). In addition, $NaHCO_3$ is particularly advantageous due to its low toxicity and ease of use. However, other suitable buffering agents may be also used. The choice of buffering agent should take into account that the particular agent needs to be both biologically compatible and possess good solubility properties in aqueous/alcohol solutions.

For reasons of price, toxicity and industrial applicability, the linear or branched $C_1$ to $C_4$ alcohol is typically ethanol. Ethanol has the further advantage of being easy to handle and also being suitable for industrial applications. Yet, apart from ethanol, other alcohols such as methanol, n-propanol or isopropanol, n-butanol, sec-butanol, isobutanol or tert-butanol are suitable for use in the presently described processes.

When ethanol is used, the ethanol is typically any pharmaceutical grade ethanol. In particular embodiments of the invention, the ethanol is a 96% pharmaceutical grade ethanol (e.g. 94% ethanol and 2% methyl ethyl ketone (MEK)). In particular embodiments of the invention the ethanol is a 95% pharmaceutical grade ethanol (3A containing 5% methanol).

To minimise coagulation factor and protease activation, the temperature of the suspension of the Apo A-I containing protein fraction (A) (such as for example Fraction IV) in buffer (B) is cooled to 1.0±0.5° C. within about 90 minutes of the buffer (B) contacting the Apo A-I containing protein fraction (A). In particular embodiments, the suspension is cooled to 1.0±0.5° C. within about 60 minutes of the buffer B contacting the Apo A-I containing protein fraction (A) (e.g. Fraction IV).

In some embodiments after the Apo A-I fraction (A) is suspended in buffer (B), the pH of the suspension is adjusted, if necessary, to be in the range from 6.4 to 10.0, such as in the range from 7.0 to 7.4, such as 7.3 or such as is in the range from 8.1 to 8.5, such as 8.3.

In order to facilitate the suspension of Apo A-I in the buffer (B), the buffer (B) can have a temperature of about 10° C. to 26° C., including about 10° C. to 16° C., such as about 13° C., when it is contacted with the Apo A-I containing protein fraction (A).

In some embodiments, the volume ratio of protein fraction (A) to buffer solution (B) is from 1:1 to 1:5, such as 1:2. The use of low volume ratios of Apo A-I fraction (A) to buffer solution (B) is particularly beneficial in industrial scale production for reducing the costs of material and storage of the buffer solution.

In some embodiments, the conductivity of the suspension is less than 5 mS/cm, such as in the range of from 0.5 to 1.0 mS/cm.

As outlined above, after solubilisation of Apo A-I containing protein fraction (A) in the buffer solution (B), impurities such as other undesired proteins or other components present in the Apo A-I protein fraction (A) are removed from the suspension, while Apo A-I proteins are kept in solution (step (b)). In some embodiments, impurities are precipitated by adding linear or branched $C_1$ to $C_4$ alcohol to an alcohol concentration of 45 to 65% (w/w), such as 50% (w/w) or 60% (w/w). This range is believed to be effective for solubilizing many protein components except for Apo A-I. This purification step therefore offers a highly specific and effective way to separate Apo A-I from other undesired components.

In order to facilitate the precipitation of impurities, the linear or branched $C_1$ to $C_4$ alcohol added to the suspension may have a temperature of about −5° C. to 30° C., such as about 5° C.

In some embodiments the linear or branched C1 to C4 alcohol is ethanol. In particular embodiments the ethanol concentration is in the range from 55% to 65% (w/w).

The pH is maintained in the range from 6.4 to 10. In some embodiments the pH is in the range from 6.4 to 9.0, including from 7.2 to 8.8, or from 8.0 to 8.6, or from 8.1 to 8.5, or from 8.2 to 8.4, or from 6.4 to 7.4.

In some embodiments, the precipitated impurities are removed from the suspension by any known process, such as filtration, centrifugation, decantation, ultrafiltration and/or sedimentation. In some embodiments, impurities are removed by filtration. In accordance with these embodiments, the filters can be chosen specifically to retain the precipitated impurities but not the desired product, e.g., not the desired Apo A-I proteins. Filters useful in such processes include polypropylene filter sheets and CH9 cellulose filter sheets.

In some embodiments, after impurities have been removed, Apo A-I is precipitated from the suspension (step (c)). This Apo A-I precipitation may be effected by adjusting the pH of the suspension to a pH in the range from 4.6 to 5.6, such as 5.4. In this pH range, precipitation of Apo A-I is believed to be highly selective, such that other undesired proteins may be kept in solution.

In some embodiments, the temperature of the suspension is adjusted (if necessary) to a range from −2 to 20° C., for precipitating Apo A-I.

In some embodiments, the Apo A-I precipitate is collected (step (d)). In accordance with these embodiments, after precipitating Apo A-I, a filter aid which facilitates the passage of the liquid through the filter may be added to the suspension. Filter aids are inorganic mineral powders or organic fibrous materials which are used in combination with filtration hardware to enhance filtration performance. Commonly encountered filter aids include diatomite, perlite and cellulose. Suitable filter aids are known in the art and include Celite™ 574 filter aid.

In some embodiments, the Apo A-I precipitate is collected by any suitable method, such as those noted above for filtration of impurities. In some embodiments, the Apo A-I precipitate is collected by filtration. In accordance with these embodiments, the filters can be chosen such that the desired Apo A-I proteins are retained, whereas other smaller components pass through the filter pores.

In specific embodiments, the process further comprises using a washing solution to remove impurities from precipitated Apo A-I. The washing solution may be water or a suitable washing buffer. If a washing step is used, the washing is carried out such that the Apo A-I proteins stay on the filter, while impurities are dissolved and washed away.

According to further specific embodiments, the process comprises a further step (e), where the collected Apo A-I precipitate is delipidated, such as through addition of alcohol for example ethanol at a concentration from within the range from about 40% to about 96% ethanol (w/w). "Delipidated" in the context of the presently described processes means the removal of lipids, thus reducing the lipid content of the Apo A-I product.

Delipidated Apo A-I precipitate (a purified Apo A-I) can be stored at or below −20° C. for a period of up to one year without loss in the proteins functionality.

The Apo A-I derived from the processes of the present invention can additionally be subject to dedicated virus reduction steps (virus inactivation and/or virus removal) to ensure virus pathogen removal. Common virus inactivation technologies include physical methods such as the classical pasteurization procedure (60° C. heating for 10 hours), short wavelength ultra-violet light irradiation, or gamma irradiation and chemical methods such as solvent detergent or low pH incubation. Virus removal technologies include size exclusion methods such as virus filtration which is also often referred to as nanofiltration. These virus filtration methods have been shown to be effective methods for removing viruses from protein solutions. In some embodiments the purified Apo A-I of the present invention is subject to a virus reduction procedure such as heat inactivation and/or virus filtration as described in EP13179755.7.

The present invention provides a purified Apo A-I characterized by the following properties:

(a) less than 0.3 mg of IgA per gram of Apo A-I;
(b) less than 0.7 mg of IgG per gram of Apo A-I;
(c) less than 0.05 mg of IgM per gram of Apo A-I;
(d) less than 4.9 mg of haptoglobin per gram of Apo A-I;
(e) less than 2.7 mg of hemopexin per gram of Apo A-I;
(f) less than 6.4 mg of fibrinogen per gram of Apo A-I;
(g) less than 0.9 mg of ceruloplasmin per gram of Apo A-I;
(h) less than 14.6 mg of albumin per gram of Apo A-I;
(i) less than 2.3 mg of alpha-2-macroglobulin per gram of Apo A-I;
(j) less than 12 mg of alpha-1-antitrypsin per gram of Apo A-I; and
(k) less than 3.9 mg of transferrin per gram of Apo A-I.

The content of the proteins can be determined by nephelometry. The Apo A-I content can also be determined using high performance capillary electrophoresis.

In another aspect of the present invention, there is provided a purified Apo A-I comprising: (a) less than 0.3 mg of IgA per gram of Apo A-I. In particular embodiments the Apo A-I preparation comprises less than 0.2 mg of IgA per gram of Apo A-I; or less than 0.1 mg of IgA per gram of Apo A-I; or less than 0.075 mg of IgA per gram of Apo A-I; or less than 0.05 mg of IgA per gram of Apo A-I; or less than 0.02 mg of IgA per gram of Apo A-I. It is advantageous to have a low IgA purity level as it can potentially affect the safety profile of pharmaceutical preparations comprising the Apo A-I preparation with lower levels desirable to minimize the risk of anti-IgA formation in IgA deficient patients. This condition is the most common primary antibody deficiency effecting about 1:133 people and as the condition is relatively mild it often goes unrecognized in effected people.

Purified Apo A-I as hereinbefore described can be formulated into pharmaceutical compositions, such as into reconstituted HDL for therapeutic use. Such pharmaceutical compositions may include a pharmaceutically acceptable carrier or diluent. Non-limiting examples of pharmaceutically acceptable carriers or diluents include water, emulsifiers, binders, fillers, surfactants, buffers, stabilizers, salts, alcohols and polyols, detergents, proteins and peptides, lipids, gums, sugars and other carbohydrates, although without limitation thereto.

Reconstituted HDL may, in addition to Apo-AI, comprise one or more of a lipid, a detergent and a stabilizer, although without limitation thereto. Non-limiting examples of lipids include phospholipids, cholesterol, cholesterol-esters, fatty acids and/or triglycerides. Preferably, the lipid is a phospholipid. Non-limiting examples of phospholipids include phosphatidylcholine (PC) (lecithin), phosphatidic acid, phosphatidylethanolamine (PE) (cephalin), phosphatidylglycerol (PG), phosphatidylserine (PS), phosphatidylinositol (PI) and sphingomyelin (SM) or natural or synthetic derivatives thereof. Stabilizers may be a carbohydrate such as a sugar (e.g. sucrose) or a sugar alcohol (e.g. mannitol or sorbitol), although without limitation thereto. If present, the detergent may be any ionic (e.g. cationic, anionic, Zwitterionic) detergent or non-ionic detergent, inclusive of bile acids and salts thereof, such as sodium cholate.

Therapeutic uses for Apo A-1 and/or reconstituted HDL formulations may include treatment or prophylaxis of cardiovascular disease (e.g. acute coronary syndrome (ACS, atherosclerosis and myocardial infarction) or diseases, disorders or conditions such as diabetes, stroke or myocardial infarction that predispose to ACS, hypercholesterolaemia (e.g. elevated serum cholesterol or elevated LDL cholesterol) and hypocholesterolaemia resulting from reduced levels of high-density lipoprotein (HDL), such as is symptomatic of Tangier disease.

EXAMPLES

As noted above, any unpurified mixture of proteins containing a substantial amount Apo A-I can be used as a starting material for the purification processes described herein.

In the following examples, Apo A-I is extracted from human plasma, using cold ethanol fractionation according to the Cohn Fractionation methods or the Kistler and Nitschmann methods, yielding plasma fraction IV-I or IV as a starting material. In step (a), the fraction IV is suspended in buffer solution (B) and then the pH adjusted prior to exposure to a higher ethanol concentration to precipitate various impurities in step (b). The impurities are removed by depth filtration in the presence of filter aid and then the pH is shifted close to the isoelectric point of Apo A-I to precipitate the Apo A-I, as step (c). Filter aid is added and the Apo A-I precipitate is collected by filtration in step (d). Optionally, the Apo A-I precipitate can be re-suspended and ethanol (e.g. 40-96% w/w) added in order to remove residual lipid, as step (e).

The Apo A-I content at various sampling points was measured using capillary electrophoresis.

Purity was expressed as a percentage, measured using capillary electrophoresis and also visually assessed on SDS-PAGE gels.

Example 1

Preparation of Fraction IV Precipitate

Human plasma was cooled to about 0° C. and adjusted to pH of about 7.2. Cold ethanol was added to a concentration of about 8% (w/w), and the temperature was lowered to approximately −2° C. The precipitate that formed (Fraction I) was removed by centrifugation or filtration.

The filtrate or supernatant from the above procedure was adjusted to about pH 6.9, and cold ethanol was added to a concentration of about 20% (w/w). The temperature was then lowered to −5° C., and the mixture was again subjected to either centrifugation or filtration. The precipitate that formed (Fraction II+III) was set aside for other purposes.

The filtrate or supernatant from the above procedure was adjusted to a pH of approximately 5, and the ethanol concentration was adjusted to about 20% (w/w). The temperature was adjusted to about −5° C. The precipitate that formed (Fraction IV) was removed by centrifugation or filtration and stored until needed in the form of a paste. This Fraction IV paste contains Apo A-I, as well as contaminating proteins and lipids.

Example 2

Factors Affecting Apo A-I Recovery from Precipitate IV

Initial experiments using a Design of Experiment (DOE) methodology focused on the dissolution of Precipitate IV (e.g., containing Fraction IV) in a sodium bicarbonate buffer, with the aim of solubilizing more ApoA-I. Table 1 summarizes the conditions of the six process parameters used for the Plackett-Burman design with centre point runs. The parameters examined included buffer volume, ethanol concentration, temperature, pH and mix time. Thirteen runs were performed on the initial screening of the Precipitate IV solubilization step.

An aliquot of Precipitate IV paste was dissolved in a volume of buffer as specified in the DOE design. The pH was then adjusted according to the DOE design after which the suspension was mixed at the temperature allocated for that run. A sample of the suspension was taken and centrifuged for fifteen minutes at 4,500 rpm. The resulting supernatant was submitted for analysis. The results of testing were normalized and expressed as g Apo A-I / L plasma.

TABLE 1

The Plackett-Burman screening design matrix
for the dissolution of Precipitate IV.

| Standard Run Order | Buffer Volume | Buffer Conc (mM) | Ethanol Conc (%) | Temp (° C.) | pH | Mix Time (min) |
|---|---|---|---|---|---|---|
| 1 | 5 | 35 | 20 | 20 | 6.4 | 1 |
| 2 | 2 | 35 | 60 | 20 | 6.4 | 4 |
| 3 | 2 | 5 | 20 | 20 | 7.2 | 4 |
| 4 | 2 | 35 | 20 | 0 | 6.4 | 4 |
| 5 | 2 | 5 | 60 | 20 | 7.2 | 1 |
| 6 | 5 | 5 | 60 | 0 | 6.4 | 1 |
| 7 | 5 | 35 | 60 | 0 | 7.2 | 4 |
| 8 | 5 | 5 | 60 | 20 | 6.4 | 4 |
| 9 | 5 | 5 | 20 | 0 | 7.2 | 4 |
| 10 | 2 | 35 | 60 | 0 | 7.2 | 1 |
| 11 | 5 | 35 | 20 | 20 | 7.2 | 1 |
| 12 | 2 | 5 | 20 | 0 | 6.4 | 1 |
| 13 | 3.5 | 20 | 40 | 10 | 6.8 | 2.5 |

Table 2 is a summary of the results obtained for the initial Plackett-Burman screening DOE where ApoA-I yield was normalized and is expressed as g ApoA-I/L plasma.

The Minitab16 DOE analysis concluded that only ethanol concentration had a $p<0.05$ for yield, where the lower the ethanol concentration in the resuspension buffer, the more solubilized ApoA-I (FIG. 1).

TABLE 2

Results for the Plackett-Burman screening design
matrix for the dissolution of Precipitate IV.

| Standard Run Order | Yield (g/L PEQ) |
|---|---|
| 1 | 0.71 |
| 2 | 0.36 |
| 3 | 1.04 |
| 4 | 0.69 |
| 5 | 0.51 |
| 6 | 0.41 |
| 7 | 0.48 |
| 8 | 0.53 |
| 9 | 0.72 |
| 10 | 0.49 |
| 11 | 0.86 |
| 12 | 0.85 |
| 13 | 0.80 |

Example 3

Effect of Ethanol Concentration and pH on Apo A-I Recovery from Precipitate IV

The study included 10 runs in which the ethanol concentration was varied between 20 and 50% and the pH between 6.4 and 7.2. The study was conducted as a duplicated $2^2$ full factorial DOE design with a center point run (Table 3). The method involved dissolving an aliquot of Precipitate IV paste in 2 parts 15 mM NaHCO$_3$ buffer with ethanol concentrations according to the DOE. The pH was then adjusted according to the DOE design after which the suspension was adjusted to a temperature of 0±1° C. and mixed for one hour. A sample of the suspension was taken and centrifuged for fifteen minutes at 4,500 rpm. The resulting supernatant was submitted for analysis. The results of testing were normalized and expressed as g ApoA-I/L plasma.

TABLE 3

The $2^2$ full factorial optimizing DOE design
matrix for the dissolution of Precipitate IV.

| Standard Run Order | Ethanol Conc (%) | pH |
|---|---|---|
| 1 | 50 | 6.4 |
| 2 | 20 | 6.4 |
| 3 | 35 | 6.8 |
| 4 | 20 | 7.2 |
| 5 | 50 | 7.2 |
| 6 | 50 | 7.2 |
| 7 | 20 | 6.4 |
| 8 | 50 | 6.4 |
| 9 | 20 | 7.2 |
| 10 | 35 | 6.8 |

Figure 2:
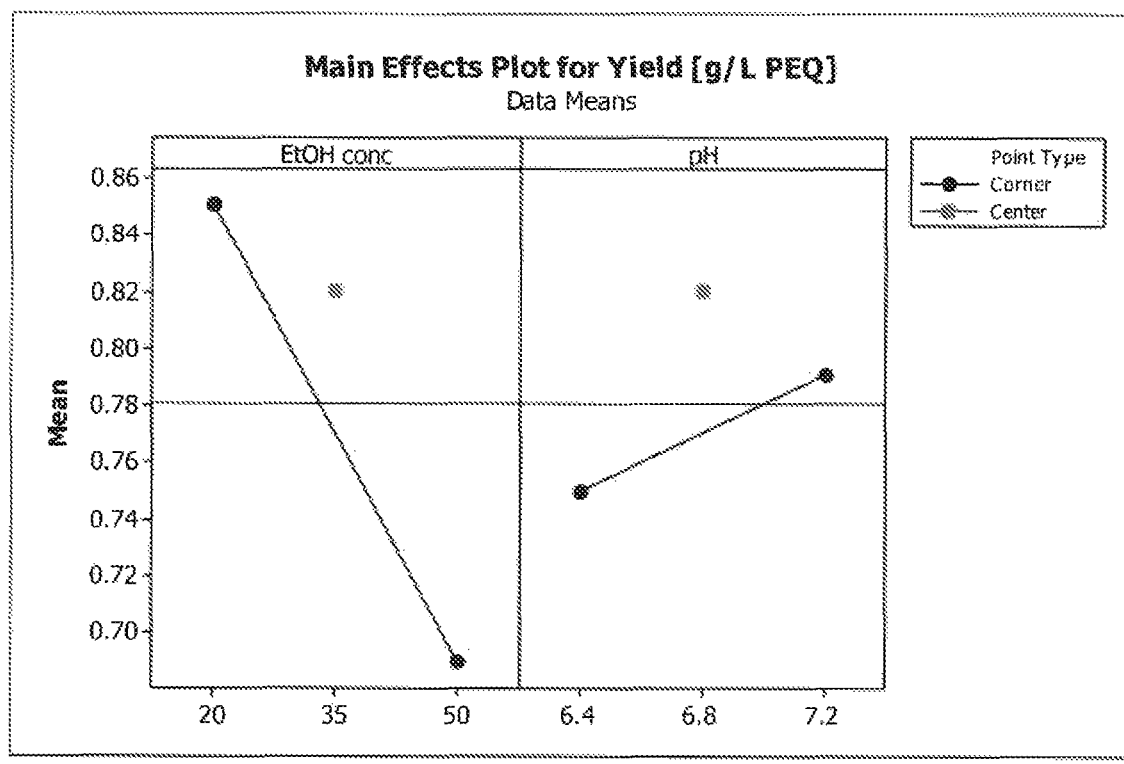
FIG. 2: Influence of ethanol concentration and pH on Apo A-I yield.

The Minitab16 DOE analysis concluded that the only factor to have a $p<0.05$ for yield was the ethanol concentration (Table 4). The results indicate that the lower the ethanol concentration in the resuspension buffer, the more solubilized ApoA-I with the greatest yield is observed when the ethanol concentration was between 20 and 30% (FIG. 2). The pH of the resuspension solution showed a minor affect with increasing the pH from 6.4 to 7.2 resulting in higher Apo A-I recoveries. However this was not found to be significant ($p=0.113$).

TABLE 4

Results for the $2^2$ full factorial optimizing
design for the dissolution of Precipitate IV.

| Standard Run Order | Yield (g/L PEQ) |
|---|---|
| 1 | 0.62 |
| 2 | 0.84 |
| 3 | 0.82 |
| 4 | 0.87 |
| 5 | 0.69 |
| 6 | 0.74 |
| 7 | 0.83 |
| 8 | 0.72 |
| 9 | 0.86 |
| 10 | 0.82 |

Figure 3:
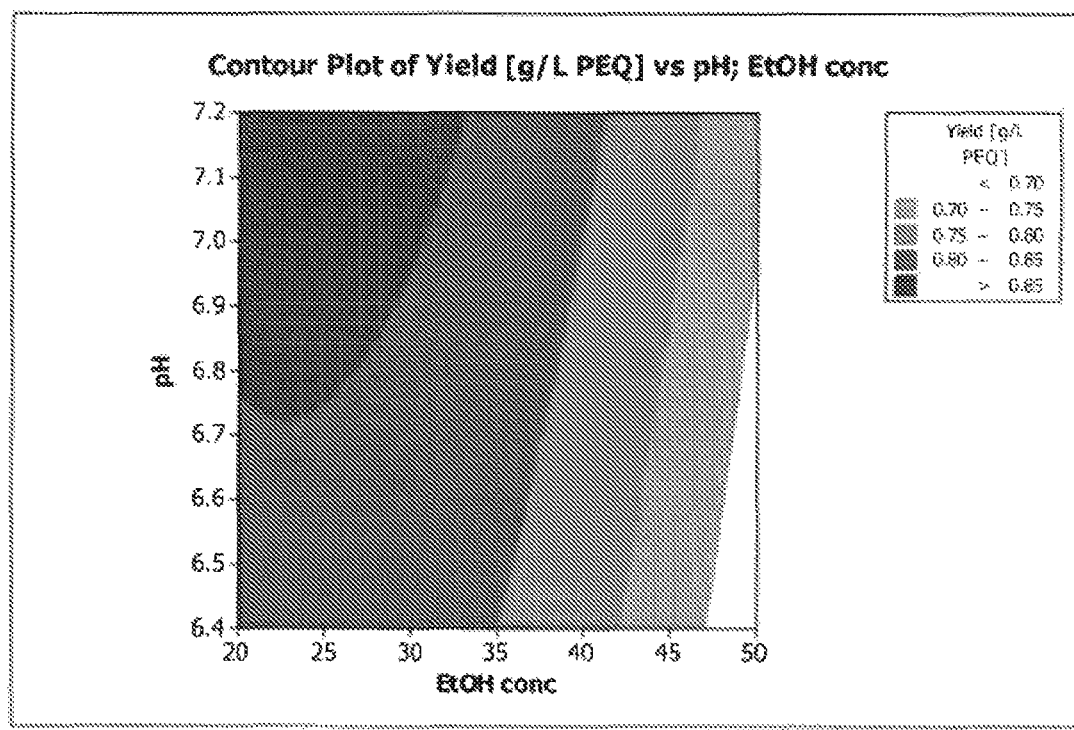
FIG. 3: Contour plot presenting the impact of ethanol concentration and pH on Apo A-I yield.

FIG. 3 further shows the influence of the pH on the Apo A-I yield when using an ethanol concentration within the range from 20 to 50%. The yield is maximized when Apo A-I is suspended in a buffer solution (B) as described herein, comprising ethanol in a concentration within the range of 15 and 30% and a pH within the range from 6.4 to 7.2.

Example 4

Effect of Ethanol Concentration on Apo A-I Recovery I from Precipitate IV

A linear experiment was performed to determine at which ethanol concentration the ApoA-I yield was maximized during the solubilization step. Ethanol concentrations of 0, 15 and 30% were tested in duplicate, as described above. Table 5 is a summary of the results obtained for the linear ethanol concentration experiment where ApoA-I yield was normalized and is expressed as g ApoA-I/L plasma and purity is expressed as a percentage.

TABLE 5

Results for the linear ethanol concentration experiment
for the dissolution of Precipitate IV.

| Standard Run Order | Ethanol Conc (%) | Yield (g/L PEQ) |
|---|---|---|
| 1 | 0 | 0.47 |
| 2 | 15 | 0.91 |
| 3 | 30 | 0.84 |
| 4 | 30 | 0.83 |
| 5 | 15 | 0.80 |
| 6 | 0 | 0.48 |

Figure 4:
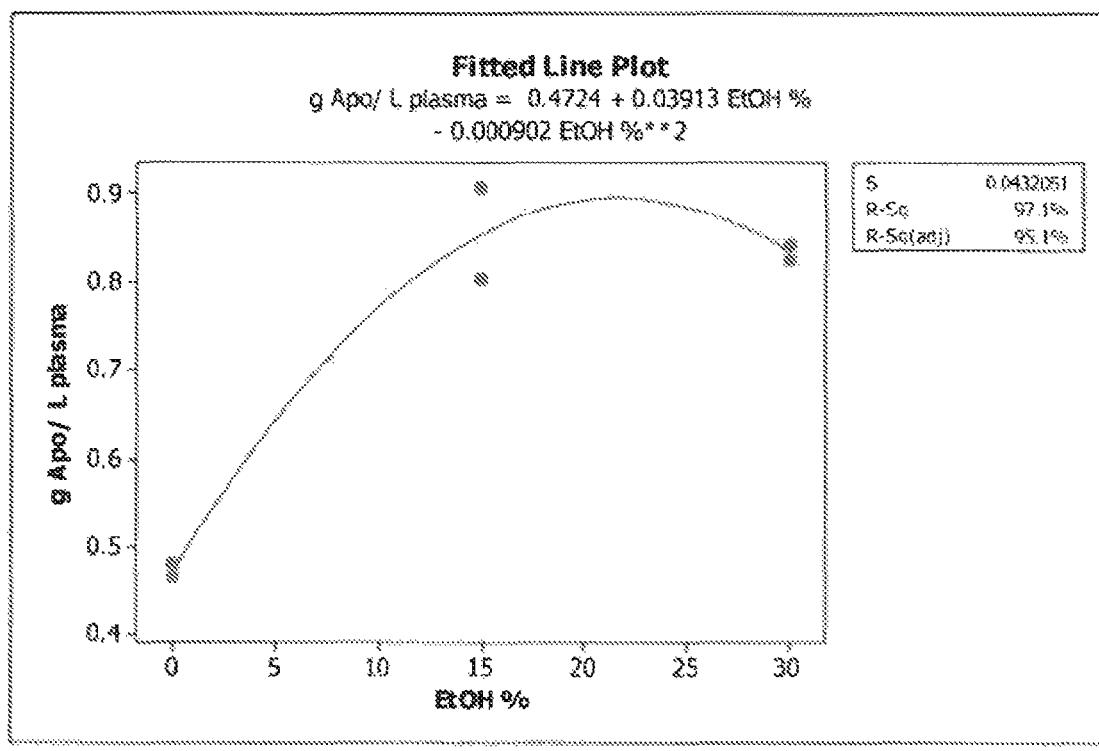
FIG. 4: Fitted line plot showing the influence of ethanol concentration on Apo A-I yield.

As shown in FIG. 4, the yield of Apo A-I obtained from plasma is maximized when using a buffer solution (B) comprising ethanol in a concentration within the range of 15 and 30%.

Example 5

Effect of Ethanol Concentration and pH on Apo A-I Recovery from Precipitate IV

Precipitate IV was dissolved in two parts suspension buffer made with 15 mM NaHCO$_3$, 0.5 mM EDTA in various ethanol concentrations according to Table 6, after which the pH was adjusted using either 0.5M HCl or 0.5M NaOH according to Table 6.

After pH setting, a sample of the suspension was taken and centrifuged for fifteen minutes at 4,500 rpm. The resulting supernatant was submitted for analysis. The results were normalized and are expressed as grams of apoA-I/L plasma.

Previous studies had shown that during the Precipitate IV re-suspension step, Apo A-I yield was maximized when an ethanol concentration of 15%-30% was used in the suspension buffer. The pH of the re-suspension was found to have only a minor effect, however the range examined was narrow, pH 6.4-pH 7.2. To determine if a broader pH range impacted Apo A-I yield, experiments were performed according to Table 6 and Apo A-I yield was calculated.

TABLE 6

Re-suspension buffer and pH conditions.

| Experiment No. | Suspension buffer | pH |
|---|---|---|
| 1470.E009.08 | 15% Ethanol | 5.0 |
| 1470.E009.09 | 15% Ethanol | 10.0 |
| 1470.E009.10 | 30% Ethanol | 5.0 |
| 1470.E009.11 | 30% Ethanol | 10.0 |
| 1470.E009.12 | 20% Ethanol | 7.4 |

The results from these experiments are presented in Table 7. At pH 5.0 the Apo A-I yield was undetectable irrespective of the ethanol concentration. Dissolution at 20% ethanol, pH 7.4 and pH 10.0 in the presence of either 15% or 30% ethanol provided similar levels of Apo A-I recovery (step b) (Table 7).

TABLE 7

Results for the ethanol concentration and pH experiment
for the dissolution of Precipitate IV.

| | Parameters | | | | |
|---|---|---|---|---|---|
| | 15% EtOH pH 5.0 | 15% EtOH pH 10.0 | 30% EtOH pH 5.0 | 30% EtOH pH 10.0 | 20% EtOH pH 7.4 |
| Yield (g APO A-I/L Plasma) | N/A | 0.72 | N/A | 0.75 | 0.73 |

N/A - undetectable levels of Apo A-I

Example 6

Protease Activity and Activated Coagulation Factors in Recovered Apo A-I

Purification of Apo A-I involving precipitation of Apo A-I and determination of proteolytic activity and the presence of activated coagulation factors in Apo A-I precipitate from step (d).

An aliquot of Precipitate IV paste was dissolved in 2 parts of a suspension buffer (B) (15 mM NaHCO$_3$/20% ethanol buffer). The suspension was adjusted to a temperature of 0±1° C. The cooling devices were programmed so that the suspension reached a target temperature of 1° C. in either 10, 65 or 120 minutes. The suspension was then mixed at that temperature (about 0±1° C.) for about one hour. Following mixing, the pH of the suspension was adjusted using either 0.5 M NaOH or 0.5 M HCl solution to yield a pH of about 7.3.

Ethanol precooled to −4° C. was added to a final concentration of 60% while maintaining the temperature of the suspension at −1 to 2° C. After the ethanol addition, the suspension was mixed for about 30 minutes.

Following the incubation, filter aid was added to the suspension. The soluble Apo A-I material (Apo A-I filtrate) was separated from insoluble impurities by filtration through a depth filter that had been pre-washed with 15 mM NaHCO$_3$/60% ethanol. The filter cake was washed with 15 mM NaHCO$_3$/60% ethanol.

An amount of 0.5 M HCl solution was added to the Apo A-I filtrate to yield a suspension having a pH of 5.4±0.1. The temperature of the suspension was adjusted to about 0° C. and the pH/temperature conditions maintained for about 2 hours.

Subsequently, filter aid was added to the suspension and the Apo A-I precipitate was collected by depth filtration. The depth filters were pre-washed with 60% ethanol. An initial post-wash with 96% ethanol was performed followed by a 20% ethanol post-wash.

The purified ApoA-I precipitate was analysed for proteolytic activity and the Non-activated partial thromboplastin time (NaPTT) clotting time was measured. These tests provide an indication as to the amount of residual protease in the Apo A-I precipitate of step (d).

To prepare the Apo A-I precipitate from step (d) for testing, it was dissolved by adding one part precipitate to three parts 2% SDS/100 mM Tris pH 8.5 buffer. Then the Apo A-I containing suspension was mixed for between 45 minutes and 1 hour. The suspension was subsequently centrifuged and the supernatant used to determine proteolytic activity and NaPTT).

The proteolytic activity assay is a colorimetric method in which the Apo A-I containing supernatant was mixed 1:3 with a buffering solution (pH 8.0). This solution was then added (200 μL) along with 20 μL of a pNA containing substrate to microtiter plate wells. The plate was then incubated at 37° C. for 10 minutes prior to an initial reading at 405 nm. The incubation was continued under the same conditions with further readings (405 nm) taken at 30, 60 and 90 minutes. At the end of the incubation the proteolytic activity (nkat/L) was calculated by measuring the amount of pNA formed between 0 and 90 minutes.

The presence of activated coagulation factors in the Apo A-I precipitate lots (from step (d)) was tested by a common non-activated partial thromboplastin time (NaPTT) assay according to Ph. Eur. monograph 2.6.22.

Figure 5:
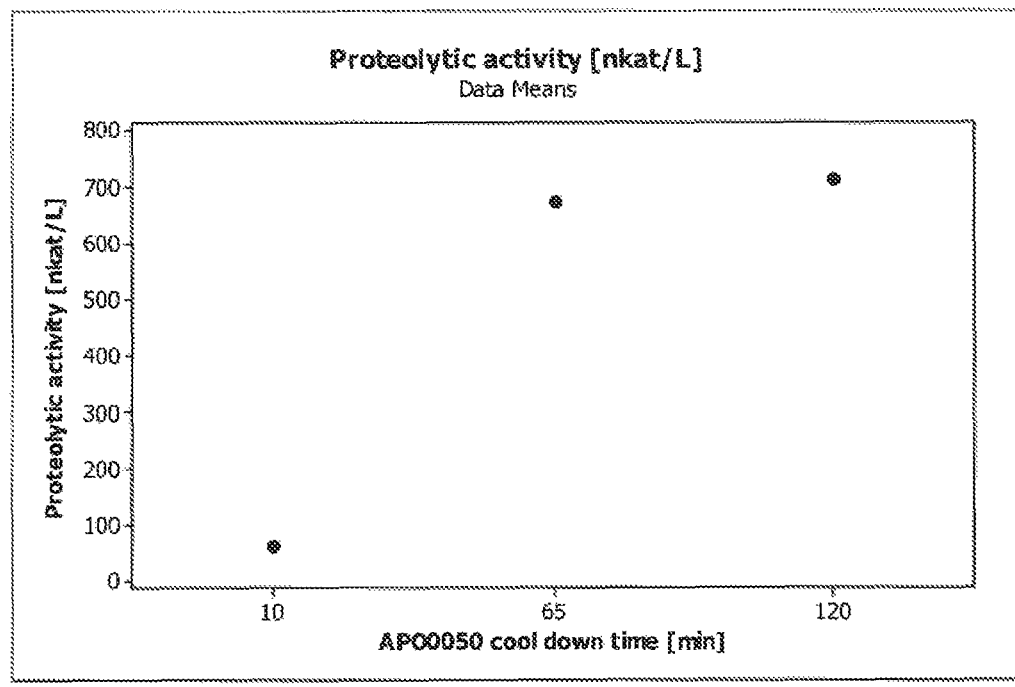
FIG. 5: Proteolytic activity (A) and Non-activated partial thromboplastin time (NaPTT) clotting time (B) in Apo A-I precipitate (step d) purified by the method described in Example 6.
Figure 5:
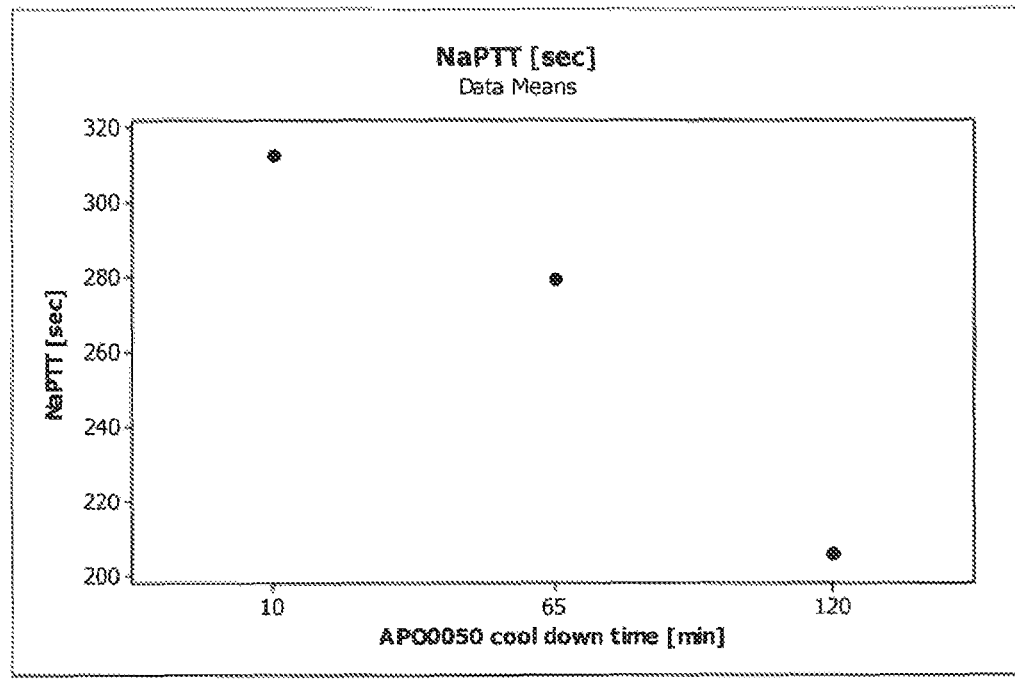

The results indicate that the levels of protease activity and activated coagulation factors in the Apo A-I precipitate (at step (d)) can be minimized by shortening the time taken to reduce the temperature to 1° C. during the resolubilization of Fraction IV, at step (a) (FIG. 5).

Example 7

Large-Scale Recovery of Apo A-I

Larger scale batches (n=17) were manufactured by dissolving Precipitate IV paste (500-550 kg) in 2 parts 15 mM NaHCO$_3$/20% ethanol buffer. The suspension was then adjusted to a temperature of 0±1° C. and mixed for about one hour. Following mixing, the pH was adjusted to 7.3 using either 0.5 M NaOH or 0.5 M HCl.

Ethanol was added up to a final concentration of 60% and the suspension mixed for about 15 minutes. The suspension was then filtered through a filter press that had been pre-washed with a 15 mM NaHCO$_3$/60% ethanol. The ensuing filter cake was also washed with a 15 mM NaHCO$_3$/60% ethanol.

The results of testing were normalized and expressed as g Apo A-I per L plasma. From 17 batches the mean recovery was 0.6 g/L (at step (b)).

Example 8

Purification of Apo A-I from Kistler-Nitschmann Fraction IV—Effect of pH During Resuspension The effect of pH in re-suspending Apo A-I from Precipitate IV on the overall yield of purified Apo A-I was evaluated by varying the pH in the range of 7.2-12.0.

The method to obtain purified Apo A-I involved dissolving Precipitate IV in two parts 20% EtOH Precipitate IV dissolution buffer containing 15 mM Sodium Carbonate (22±2° C.). After addition of the buffer to the Precipitate IV, the suspension temperature was lowered to 2° C. (2±1° C.) in about 15 minutes. After mixing for approximately 15 minutes the pH of the suspension was adjusted to the target pH in the range of 7.2 to 12.0 prior to 96% ethanol being added to achieve a final concentration of 60%.

The ensuing suspension was filtered in the presence of Celite 574. The pH of the Filtrate was then lowered to about pH 5.3 and incubated for about 2 hours at about 0° C. Filter aid was then added, the suspension mixed for about 30 minutes before being filtered and the Apo A-I precipitate collected. The Apo A-I precipitate was then delipidated with 96% ethanol.

To determine the Apo A-I content and other characteristics of the delipidated Apo A-I precipitate the precipitate was dissolved at room temperature for 45 minutes in 3 parts 100 mM Tris buffer, pH 8.5 containing 2% SDS. The samples were centrifuged prior to analysis.

The influence of the pH at the Precipitate IV Resuspension step on overall Apo A-I yield in the delipidated Apo A-I precipitate was investigated with higher recovery levels obtained when using higher pH extraction conditions (Table 8). The amount of Apo A-I was determined using high performance capillary electrophoresis (Hewlett Packard 3D CE, Agilent Technology). The determination is performed under denaturing conditions, that is, in the presence of SDS. Apo A-1 content can then be determined in both aqueous and in lipid containing samples (e.g. reconstituted HDL). Briefly, samples (150 μL) containing approximately 2-3 mg/mL Apo A-I (if necessary diluted with water) were prepared with 16% SDS (25 μL) and phenylalanine (25 μL, 2 or 4 mg/mL). The samples were then incubated in a boiling water bath for 3 minutes prior to 1:2.5 dilution in a electrophoresis buffer (50 mM sodium borate, 0.2% SDS, pH 9.1, 300 μL) and filtered (0.45 μm). The samples were then loaded onto a fused silica capillary (56 cm by 50 m id, Agilent G1600-61232). Electrophoresis was carried out at 25 kV. The standard used was an International Apo A-I Standard (BCR-393) and a standard curve established from 20 to 950 μg/mL. Quantification is based on the relative peak areas in comparison with the internal standard (Phenylalanine).

TABLE 8

Yield of purified Apo A-I (grams per liter plasma) as a function of the pH used to extract Apo A-I from Fraction IV.

| Production batches | pH 7.3 | pH 8.1 | pH 8.3 | pH 8.4 | pH 8.5 | pH 8.7 |
|---|---|---|---|---|---|---|
| Yield | 0.22 | 0.28 | 0.37 | 0.53 | 0.51 | 0.50 | 0.56 |

The level of other plasma proteins in the purified Apo A-I preparation (mg of plasma protein per gram of Apo A-I) were determined by nephelometry (BN ProSpec, Siemens) with references, control and antiserum obtained from Siemens. For the IgA content an N latex IgA kit from Siemens was used in accordance with the manufacturer's instructions.

The level of other plasma proteins in the purified Apo A-I preparations remained stable until the pH of the Fraction IV extraction step reached pH 8.5. At higher pH extraction conditions, such as pH 8.7, the levels of the plasma proteins increased (Table 9).

TABLE 9

Impurity levels in purified Apo A-I as a function of the pH used to extract Apo A-I from Fraction IV.

| Plasma protein (mg/g Apo A-I) | pH 7.3 | pH 8.1 | pH 8.3 | pH 8.5 | pH 8.7 |
|---|---|---|---|---|---|
| Albumin | <10.1 | <9.1 | <10.2 | <8.8 | 13.7 |
| Alpha-1-antitrypsin | 2.1 | 8.1 | 9.5 | 10.8 | 46.7 |
| Alpha-2-macroglobulin | <1.4 | <1.2 | <1.4 | <1.2 | <1.4 |
| Ceruloplasmin | <0.6 | <0.5 | <0.6 | <0.5 | <0.6 |
| Fibrinogen | <4.6 | <4.1 | <4.6 | <4.0 | <4.5 |
| Haptoglobin | <2.3 | <2.0 | <2.3 | <2.0 | 5.4 |
| Hemopexin | <1.6 | <1.4 | <1.6 | <1.4 | 2.2 |
| IgA | 0.02 | 0.03 | 0.06 | 0.2 | 0.7 |
| IgG | <0.1 | <0.1 | 0.15 | 0.6 | 3.4 |

TABLE 9-continued

Impurity levels in purified Apo A-I as a function of the pH used to extract Apo A-I from Fraction IV.

| Plasma protein (mg/g Apo A-I) | pH 7.3 | pH 8.1 | pH 8.3 | pH 8.5 | pH 8.7 |
|---|---|---|---|---|---|
| IgM | 0.03 | 0.03 | 0.03 | 0.03 | 0.03 |
| Transferrin | <2.6 | <2.4 | <2.6 | 3.0 | 15.4 |

The invention claimed is:

1. A process of obtaining Apo A-I from an Apo A-I containing protein fraction (A), comprising:
   (a) suspending the Apo A-I containing protein fraction (A) in a buffer solution (B) comprising 15 to 30% (w/w) of a linear or branched C1 to C4 alcohol to form a suspension comprising solubilized Apo A-I, wherein the suspension has a pH in the range from 6.4 to 10.0,
   (b) removing impurities from the suspension while keeping the Apo A-I solubilized,
   (c) precipitating Apo A-I from the suspension, and
   (d) collecting the Apo A-I precipitate.

2. The process of claim 1, wherein the buffer solution (B) comprises 20% (w/w) of the linear or branched C1 to C4 alcohol.

3. The process according to claim 1, wherein the suspension comprising solubilized Apo A-I has a pH in the range from 7.2 to 8.8.

4. The process according to claim 1, wherein the suspension comprising solubilized Apo A-I has a pH in the range from 8.1 to 8.5.

5. The process according to claim 1, wherein the suspension comprising solubilized Apo A-I has a pH in the range from 7.0 to 7.6.

6. The process according to claim 1, wherein the buffer solution (B) comprises 5 mM to 35 mM $NaHCO_3$.

7. The process according to claim 1, wherein the linear or branched C1 to C4 alcohol is ethanol.

8. The process according to claim 1, wherein in step (a), the volume ratio of Apo A I protein fraction (A) to buffer solution (B) is from 1:1 to 1:5.

9. The process according to claim 1, wherein the conductivity of the suspension comprising solubilized Apo A-I formed at step (a) is less than 5 mS/cm.

10. The process according to claim 1, wherein in step (b), impurities are removed by precipitation by adding linear or branched C1 to C4 alcohol to an alcohol concentration of 55 to 65% (w/w).

11. The process according to claim 10, wherein in step (b) the linear or branched C1 to C4 alcohol added to the suspension has a temperature of about −5° C. to 15° C.

12. The process according to claim 1, wherein in step (b), impurities are removed by precipitation followed by filtration, centrifugation, decantation, ultrafiltration and/or sedimentation.

13. The process according to claim 1, wherein in step (c), the pH of the suspension is adjusted to be in the range from 4.6 to 5.6.

14. The process according to claim 1, wherein in step (c), the temperature of the suspension is adjusted to be in the range from −2 to 20° C. to precipitate Apo A-I.

15. The process according to claim 1, further comprising step (e), comprising delipidating the collected Apo A-I precipitate by adding ethanol in an amount within the range from 40 to 96% (w/w).

16. A method of producing a pharmaceutical composition, comprising producing Apo A-I according to the method of claim 1 and combining the Apo A-I with a pharmaceutically acceptable carrier or diluent.

17. A method of producing reconstituted HDL, comprising producing Apo A-I according to the method of claim 1 and combining the Apo A-I with a lipid to thereby produce reconstituted HDL.

18. A method of producing a pharmaceutical composition, comprising producing Apo A-I according to the method of claim 1; combining the Apo A-I with a lipid to thereby produce reconstituted HDL; and combining the reconstituted HDL with a pharmaceutically acceptable carrier or diluent to thereby produce the pharmaceutical composition.

* * * * *